United States Patent [19]

Marshall et al.

[11] Patent Number: 5,606,976
[45] Date of Patent: Mar. 4, 1997

[54] METHOD AND APPARATUS FOR UNIFYING THE VENTILATION/PERFUSION AND PRESSURE/FLOW MODELS

[75] Inventors: Bryan E. Marshall; Carol Marshall, both of Wynnewood; C. William Hanson, Radnor; Fred Frasch, Glenside, all of Pa.; Carl Medsker, Mt. Laurel, N.J.

[73] Assignee: Trustees of the University of Pennsylvania, Philadelphia, Pa.

[21] Appl. No.: 280,294

[22] Filed: Jul. 26, 1994

[51] Int. Cl.⁶ ................................................ A61B 5/0205
[52] U.S. Cl. ............................................ 128/671; 128/716
[58] Field of Search ....................................... 128/668, 670, 128/671, 672, 713, 716, 720, 725

[56] References Cited

U.S. PATENT DOCUMENTS 4,796,639  1/1989  Snow et al. ............................. 128/671
5,003,976  4/1991  Alt ........................................... 128/671

*Primary Examiner*—Angela D. Sykes
*Assistant Examiner*—Eric F. Winakur
*Attorney, Agent, or Firm*—Duane, Morris & Heckscher

[57] ABSTRACT

A method and apparatus for unifying the pressure/flow and ventilation perfusion ratios is disclosed. The method comprises the following steps: determining the initial health condition of a patient so as to define a pulmonary pressure flow curve for each of a plurality of lung compartments of said patient; applying a stimulus of hypoxic pulmonary vasoconstriction to the pressure flow curve for each compartment to obtain a pressure flow curve for each of said plurality of compartments; and deriving a pulmonary artery pressure value corresponding to a ventilation/perfusion ratio that satisfies both the individual and total pressure flow requirements for said pulmonary pressure/flow curves.

11 Claims, 7 Drawing Sheets

METHOD AND APPARATUS FOR UNIFYING THE VENTILATION/PERFUSION AND PRESSURE/FLOW MODELS

FIELD OF THE INVENTION

The present invention is directed to methods and apparatus for facilitating medical treatment in the area of respiratory intensive care. In particular, the present invention is directed to methods and apparatus for determining, from physiological data, the causes of pulmonary failure, and to quantify the effects of hypoxic pulmonary vasoconstriction (HPV) on lung function.

BACKGROUND OF THE INVENTION

In the prior art, two separate techniques have been utilized for the clinical treatment and physiological examination of lung function. The first technique measures pulmonary gas exchange and is referred to as the "multiple inert gas technique" (MIGT). Pulmonary gas exchange can be analyzed by the distribution of ventilation/perfusion ratios ($V_A/Q$). In this type of analysis, the lung is conceptually divided into as many as 50 compartments, each having discrete $V_A/Q$ ratios. In practice, the distribution of flow and ventilation to the 50 compartments (the $V_A/Q$ ratio) is derived from the steady state elimination of six inert gases infused in solution at a constant rate. When the $V_A/Q$ ratio is expressed logarithmically, the distribution approaches a normal one such that the gas flow and ventilation can be described by their respective averages and standard deviations.

In 1977, Wagner and West published a computer program entitled "Pulmonary Gas Exchange" which calculated the pulmonary gas exchange from $V_A/Q$ distributions generated by the multiple inert gas technique (MIGT). The MIGT technique is not useful in acute clinical situations, because it produces a static picture of the pulmonary system. For example, the MIGT analysis does not permit prediction of changes, such as those caused by the administration of fluids and medications to the patient. Measuring pulmonary gas exchange to analyze respiratory problems, therefore, has a number of limitations resulting from its static nature.

A second method for analyzing the function of a lung is to evaluate pulmonary circulation, or the distribution of blood flow to the lung. This evaluation relies upon changes in blood flow with respect to changes in lung blood pressure. The pressure/flow relationship was first analyzed in detail by Fung, et al. in their study of the characteristics of cat lung tissue. Fung's measurements of all the properties and dimensions of cat pulmonary vessels showed that the nature of the pressure/flow relationship was attributable to the elastic nature of the vessel walls. The properties of the vessels were generalized and extended to provide a model of pulmonary circulation that permitted the generation of pressure/flow curves for any combination of pathologic or physiological changes (Marshall et al.).

However, the predominant issue in respiratory intensive care is the simultaneous achievement of adequate pulmonary gas exchange and steady-state hemodynamics. Abnormal values are expected and many of the therapeutic measures have been derived empirically and are applied by individual trial. The development of sophisticated monitoring tools has permitted success in the management of these complex disease states. However, the pathophysiological relationship between gas exchange and pulmonary blood flow remains obscure.

It is, for example, understood that because ventilation/perfusion ratios are determined by regional perfusion characteristics and that hypoxic pulmonary vasoconstriction (HPV) is the only known local vascular feedback control mechanism, HPV must actively regulate the $V_A/Q$ distribution. While this interaction has been recognized, no systematic quantification has been advanced for clinical or experimental applications.

Prior researchers have typically looked to the excessive number of influencing variables and retreated to interpret the changes in conceptual terms. These approaches have not included analysis of critical mechanisms, and have led to the acceptance of sometimes erroneous or misleading interpretations.

The present invention is directed to a novel analysis of the relationship between gas exchange and pulmonary flow as they impact on pulmonary intensive care. The present invention identifies the quantitative effects of the principal variables involved in pathophysiologic situations encountered clinically and particularly to evaluate the role of HPV in this relationship. The present invention combines the ventilation/perfusion ratio distribution with the pressure flow model to provide a more comprehensive method for analyzing lung function. The bridge between the above two inter-related aspects of lung function is HPV.

The present invention is specifically directed to the evaluation and treatment of patients undergoing acute pulmonary distress in an intensive care unit (ICU). Selected data from the patient's monitoring device are entered into a computer program in accordance with the present invention. The system analyzes all of the data and outputs both the best estimate of the underlying cause of the patient's distress as well as suggestions as to the next treatment step.

SUMMARY OF THE INVENTION

In accordance with the present invention, a method for combining the ventilation/perfusion ratios and pressure/flow relationships of a patient comprising the following steps: determining the initial health condition of a patient so as to define a pulmonary pressure flow curve for each of a plurality of lung compartments of said patient and for the total lung; applying a stimulus of hypoxic pulmonary vasoconstriction to the pressure flow curve for each compartment to obtain a pressure flow curve for each of said plurality of compartments; and deriving a pulmonary artery pressure value corresponding to a ventilation/perfusion ratio that satisfies both the individual compartment and total lung pressure flow requirements for said pulmonary pressure/flow curves.

In a more preferred embodiment, the present invention is directed to a method for combining the ventilation/perfusion ratio and the pulmonary artery pressure for a patient comprising the following steps: determining the fractional flow of blood to each of a plurality of lung compartments of said patient; said fractional flow being based upon the ventilation/perfusion ratios for each of said plurality of lung compartments; determining the total cardiac output of said patient; calculating the actual blood flow to each of said plurality of compartments, said actual blood flow equalling the total cardiac output multiplied by the fractional flow of blood to each compartment; determining the alveolar and capillary blood oxygen partial pressures for each of said plurality of compartments; determining the stimulus for hypoxic pulmonary vasoconstriction for each of said plurality of compartments and the overall gas exchange value for the entire lung of said patient; determining the pressure/ flow relationship based upon said stimulus for hypoxic pulmonary vasoconstriction; calculating a total cardiac output for the patient in the absence of hypoxic pulmonary vasoconstriction; and determining a pulmonary artery pressure such that the normal blood flow to each said compartment equals the summation of the compartmental blood flows.

In yet a further embodiment, the present invention is directed to a method for linking the ventilation/perfusion ratios and the pressure/flow model of a patient comprising the following steps: determining the fractional flow of blood to each of a plurality of lung compartments based upon an average and logarithmic standard deviation for the ventilation/perfusion ratio for each of a plurality of compartments of a lung; measuring the total cardiac output of a patient; determining the actual blood flow to the patient's lung as equalling the total cardiac output multiplied by the fractional flow; determining the alveolar and capillary blood pressures of each of said lung compartments; determining the stimulus for hypoxic pulmonary vasoconstriction for each of said plurality of lung compartments; determining the overall gas exchange for the entire lung; determining the pressure/flow relationship based upon said stimulus for hypoxic pulmonary vasoconstriction; calculating a total cardiac output for said patient in the absence of hypoxic pulmonary vasoconstriction; determining a pulmonary artery pressure such that the normal blood flow to each said compartment equals the summation of the blood flowing to each of said compartments.

In still a further embodiment, the present invention is directed to a method for combining the ventilation/perfusion ratio and the pressure flow for a patient in pulmonary distress: determining the fractional flow of blood to each compartment of approximately 49 lung compartments based upon an average and standard deviation for the logarithm of the ventilation/perfusion ratio for each of said compartments, and the pulmonary artery pressure of said lung; determining the actual blood flow to said lung as equalling the total cardiac output times said fractional flow; determining the stimulus for hypoxic pulmonary vasoconstriction for each of said lung compartments and the overall gas exchange for the entire lung; determining the pressure/flow relationship for said patient based upon the stimulus for hypoxic pulmonary vasoconstriction and the state of the vasoconstriction, determining a total cardiac output in the absence of hypoxic pulmonary vasoconstriction; altering the pulmonary artery pressure of said patient using a vasodilator such that the summation of the cardiac output for each compartment equals total blood flow.

The present invention is also directed to an apparatus for defining a pulmonary artery pressure comprising: first monitor means for measuring the ventilation/perfusion ratio for each of a plurality of lung compartments for a patient; second monitor means for determining the cardiac output of a patient; processor means under the control of a prestored computer program for determining the fractional blood flow to each of said lung compartments, the stimulus for hypoxic pulmonary vasoconstriction of each of said plurality of lung compartments, the pressure and flow equation for each of said compartments; memory means for storing said fractional blood flow, said stimulus for hypoxic pulmonary vasoconstriction, and said pressure and flow equation for said compartments and the normal cardiac output value of said patient; said processor further determining the relative flow of blood to said lung compartment as a ratio of the actual flow of blood, and determining a value for relative flow such that the sum of the normal flow times said ratio equals total flow, said value for relative flow being a function of pulmonary artery pressure.

DETAILED DESCRIPTION OF THE PRESENT INVENTION

The present invention is described with reference to the enclosed Figures wherein the same numbers are utilized where applicable. In a broadest embodiment, the present invention is directed to a method and apparatus for linking the ventilation/perfusion and pressure-flow models of lung function in order to determine a precise point at which the pulmonary artery pressure for the patient is equal for both models. The determination of this point can facilitate prompt pulmonary care and can indicate the proper course of treatment for pulmonary patients in distress, particularly in the intensive care context. The present invention includes hypoxic pulmonary vasoconstriction (HPV) which is the principle biofeedback mechanism which regulates pulmonary blood flow and ventilation/perfusion ratios.

Figure 1:
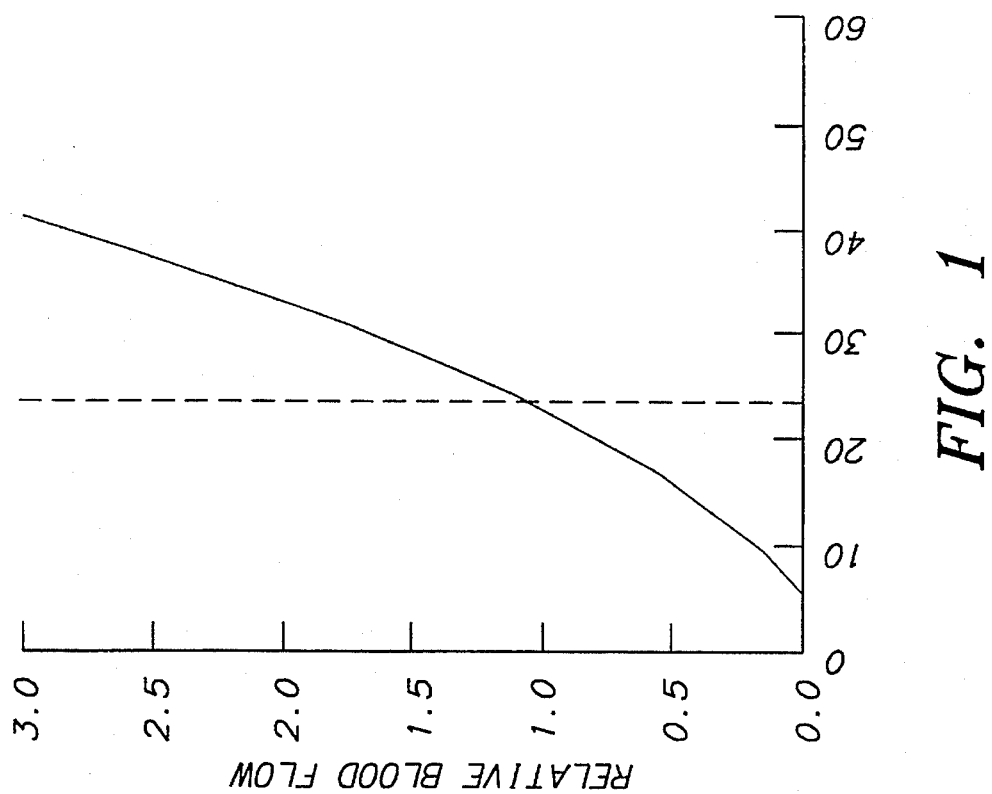
FIG. 1 illustrates relative blood flow verses initial pulmonary artery pressure.

Referring to FIGS. 1 to 4, the theoretical model which underpins the method and apparatus of the present invention is shown and described. This theoretical model is premised upon a number of initial variables which impact upon lung function and is explained in the context of the MIGT method. Referring initially to FIG. 1, initial general conditions such as cardiac output, left atrial pressure, alveolar pressure, pleural pressure and hematocrit are measured for the patient so as to define a single pulmonary artery pressure, in the absence of hypoxic pulmonary vasoconstriction (HPV). For each of 49 compartments, the alveolar and mixed venous oxygenation are then derived.

Figure 4:
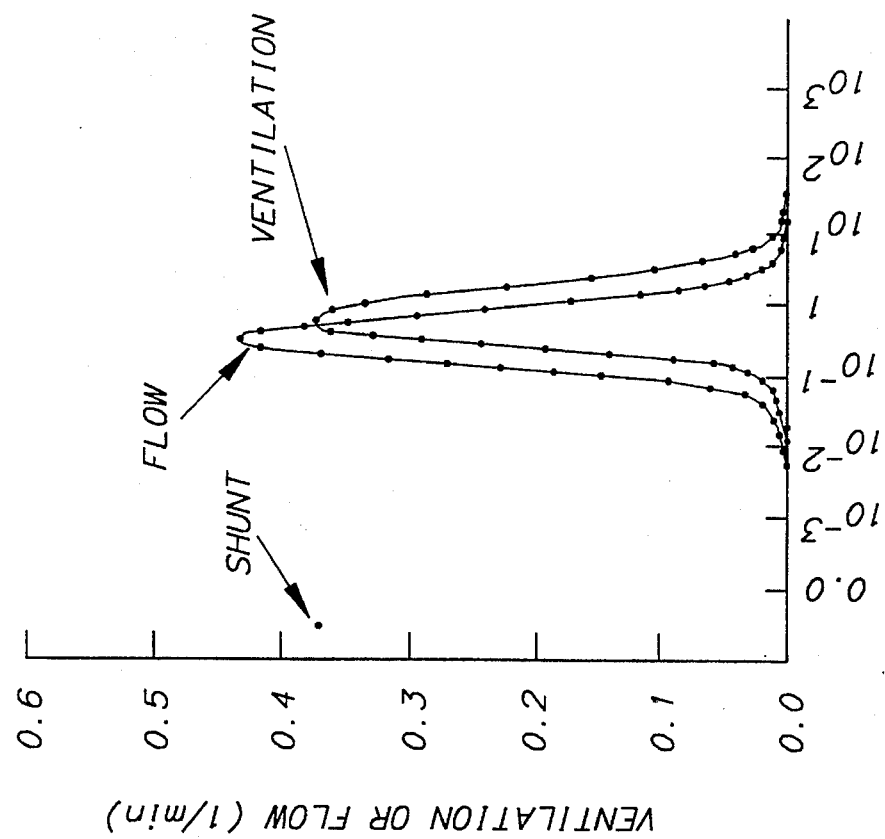
FIG. 4 is the compartment $PSO_2$.

From each of these values, the local stimulus for hypoxic pulmonary vasoconstriction ($PSO_2$) is calculated for each of the 49 compartments. The stimulus of hypoxic pulmonary vasoconstriction represents the point at which hypoxic pulmonary vasoconstriction is induced. As shown in FIG. 1, the compartmental $PSO_2$ from FIG. 4 is applied to the pressure flow curve of FIG. 3 to obtain a pressure flow curve for each compartment that now includes HPV. There is only one pulmonary artery pressure value that satisfies both the individual and total flow requirements for the curve.

Figure 2:
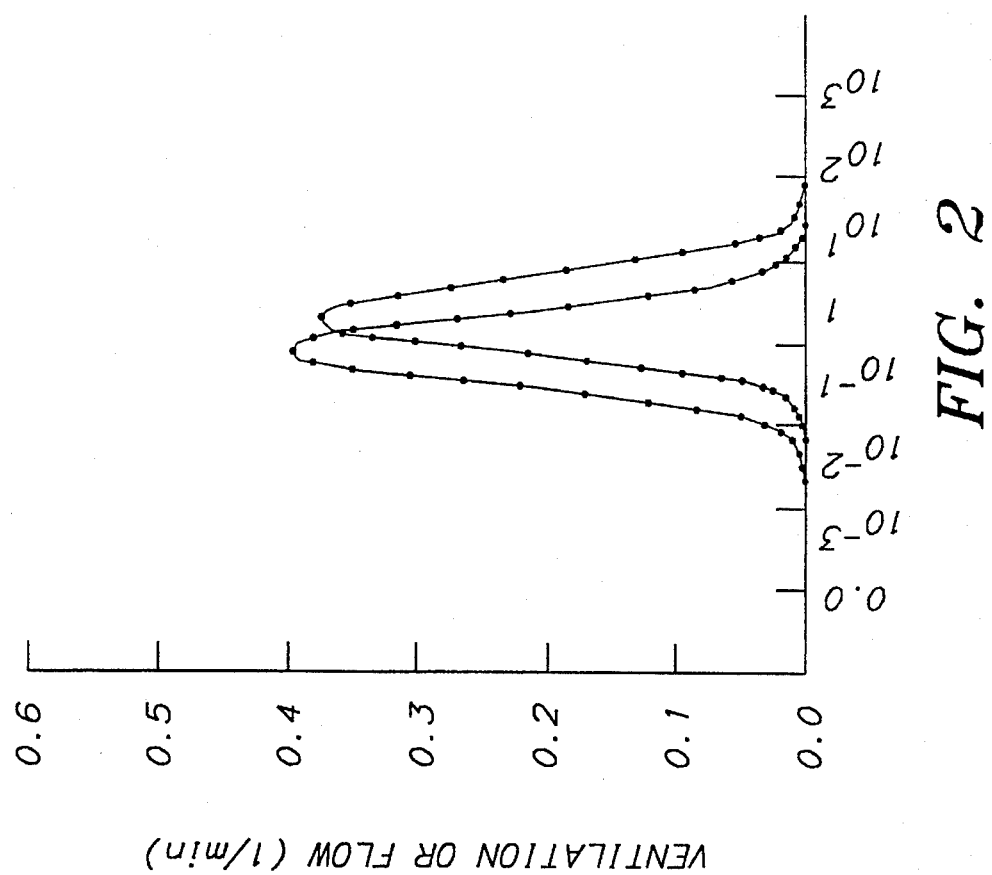
FIG. 2 illustrates the change in pulmonary artery pressure caused by HPV.
Figure 3:
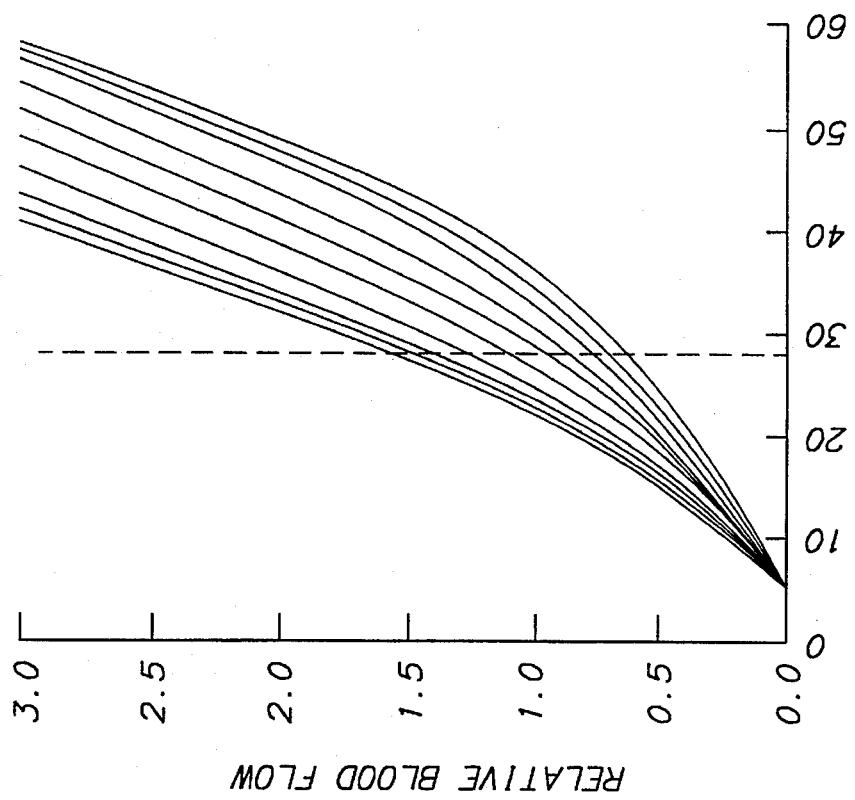
FIG. 3 illustrates the pressure flow curves for each compartment including HPV.

Referring now to FIG. 2, because the presence of HPV has altered the distribution of blood flow, a new pair of ventilation/perfusion ($V_A/Q$) curves is generated. The blood flow and $V_A/Q$ to each compartment is altered and the procedure illustrated in FIGS. 3 and 4 is repeated iteratively until the solution converges such that the change in arterial oxygen tension is less than 0.1% with the final iteration. The starting conditions for the patient in the absence of HPV are shown in FIG. 4 and the final results in the presence of HPV are shown in FIG. 2. These Figures illustrate the correlation between the ventilation/perfusion and pressure/flow models. The calculation can proceed in either direction.

Figure 6:
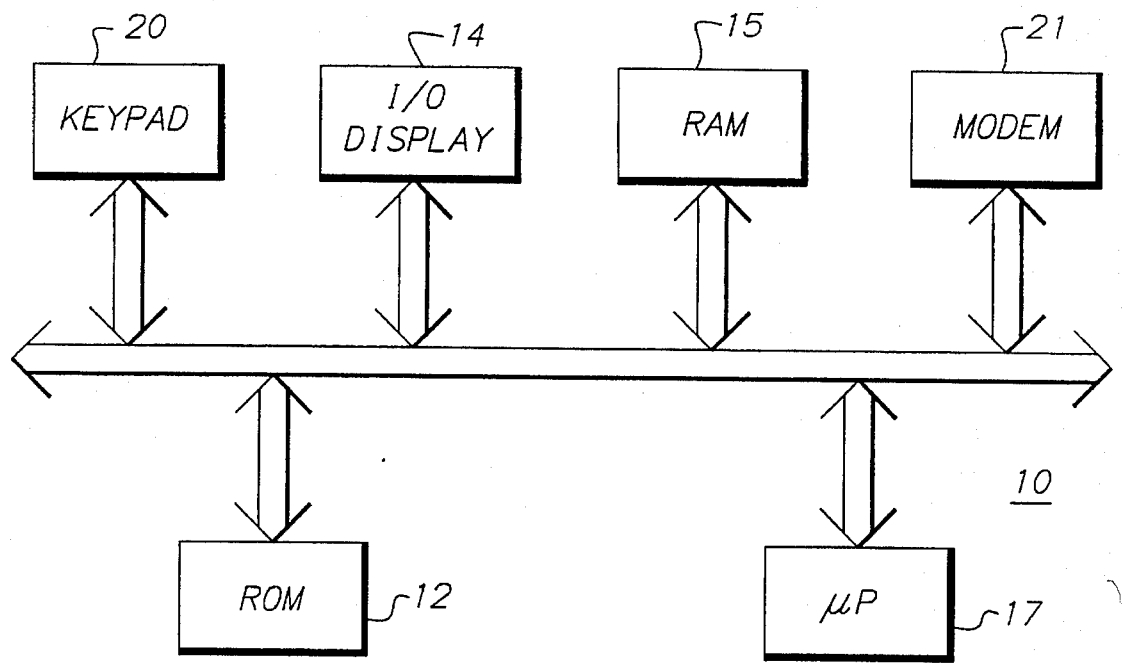
FIG. 6 is a block diagram of a more preferred apparatus embodiment in accordance with the present invention.
Figure 5:
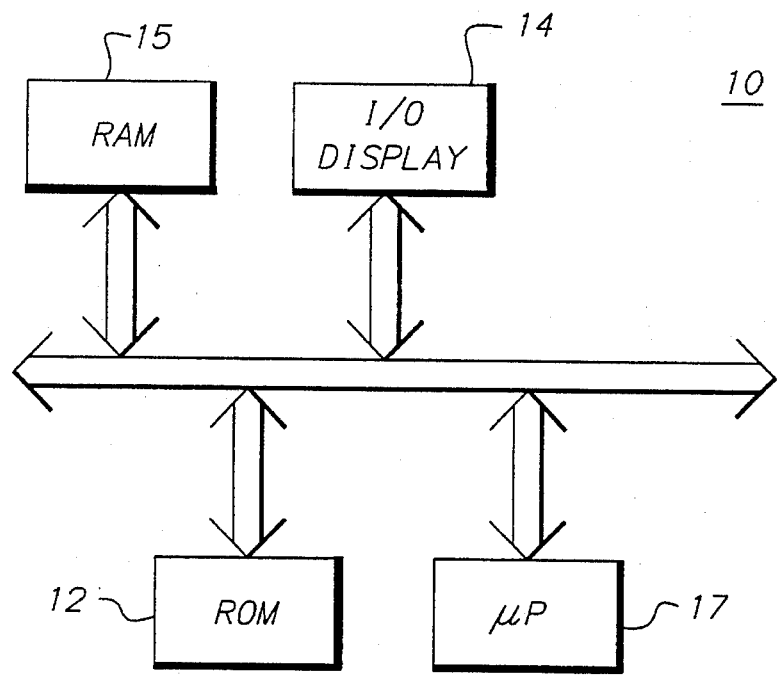
FIG. 5 is a flow diagram of a simplest apparatus in accordance with the present invention.

Referring to FIGS. 5 and 6, embodiments of an apparatus for implementing the theory of the present invention are shown and described. The apparatus facilitates the intensive care unit treatment of a patient in pulmonary distress. As shown in FIG. 5, the apparatus 10, in a simplest embodiment, comprises a microprocessor-based system which includes a memory such as a ROM 12, an input/output device 14, a RAM 15 and a microprocessor 17. Input/output device 14 facilitates the entry of patient data and parameters. A prestored program in ROM 12 is used in the present invention to be described below. The input/output device 14, in a preferred embodiment, may confuse with a graphical user interface system such as Microsoft WINDOWS® as well as an expert software package stored in ROM 12.

In a preferred embodiment, interface 14 receives information regarding tests, drugs, patient history, and examination data. A relational database is stored in ROM 12 which includes data representing the criteria for a plurality of normal lungs of varying dimensions.

The present invention in the more preferred embodiment of FIG. 6 may include a user/system interface 18 such as keypad 20 which permits the input variables from the querying of hypotheticals, the submission of physician advice and predictions, graphical renderings of the lung, case retrievals, trends and patient summaries. A modem 21 may be used to transmit and receive data.

Figure 10A:
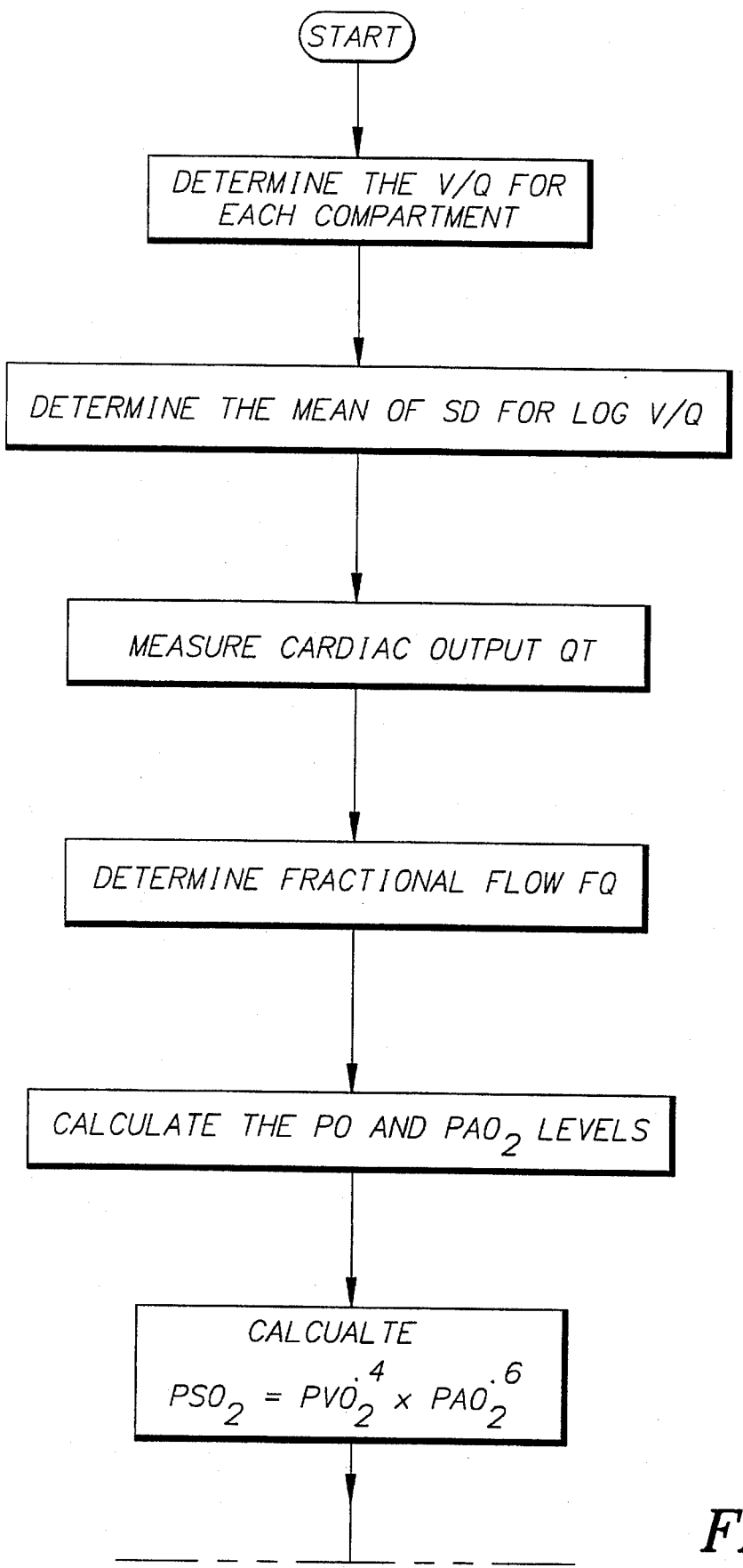
FIGS. 10A and 10B are an algorithmic representation of the operation of the present invention.
Figure 10B:
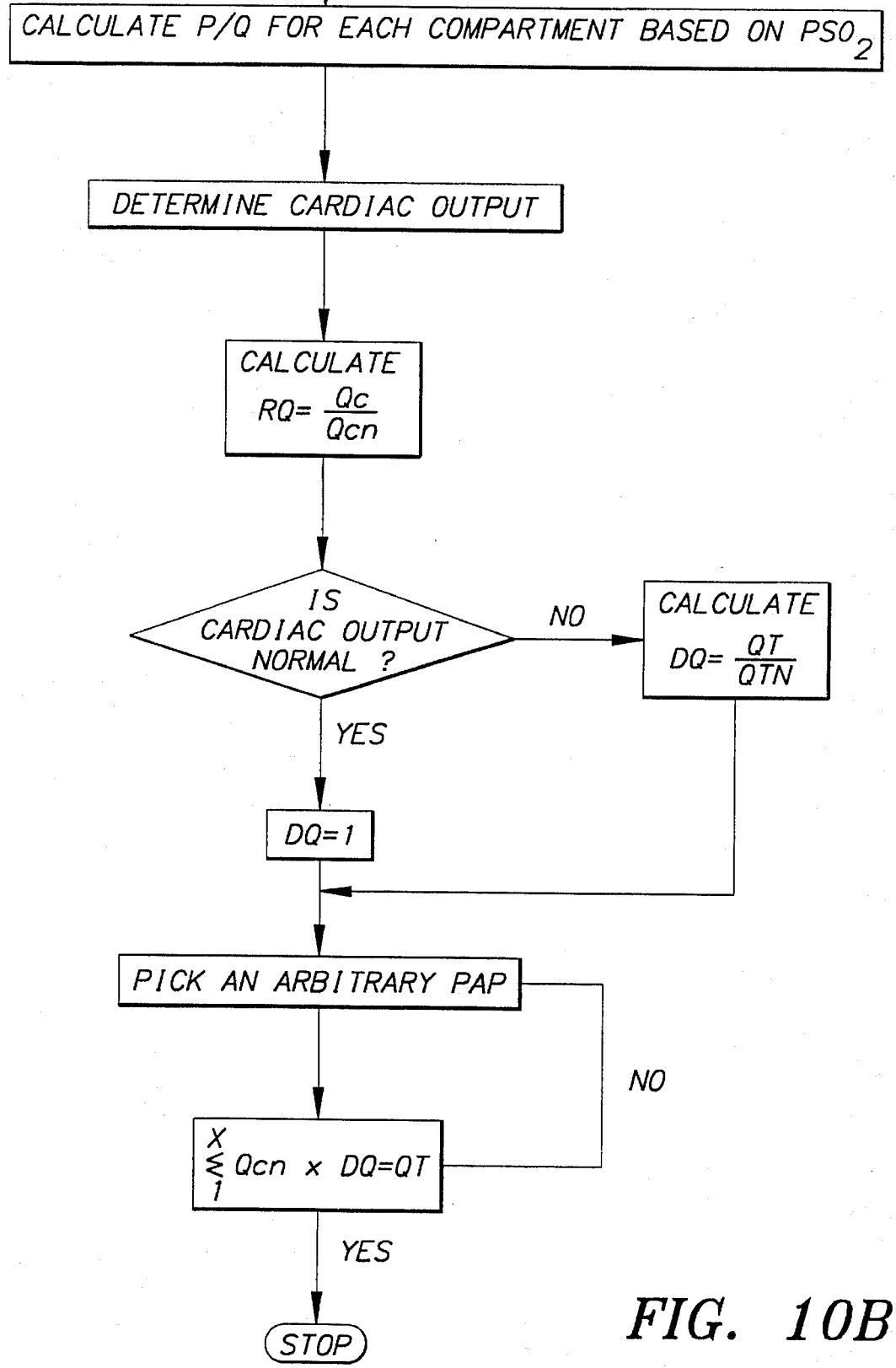

Referring now to FIG. 10, an algorithmic representation of a prestored computer program in accordance with the present invention is shown and described. The algorithm which is grounded in the principle shown in FIGS. 1–4, is directed to a method and apparatus for unifying the ventilation/perfusion and pressure/flow models of lung function and is stored in ROM 12.

Initially, based upon the patient's size, weight and lung capacity, a model of a normal patient's cardiac output and actual blood flow is determined using data stored in memory such as RAM. Using the MIGT technique, a mean and standard deviation for the logarithm of $V_A/Q$ for each of the lung's 50 compartments is calculated and stored. From this value, the fractional blood flow (FQ) to each lung compartment is derived.

Using the $V_A/Q$ model, the flow and ventilation to the 50 compartments of differing $V_A/Q$ ratios is derived. These values are derived from a steady-state elimination of six inert gases infused in solution at a constant rate (MIGT). The model comprises two extremes (anatomic dead space wherein $V_A/Q$ approaches infinity and pure shunt where $V_A/Q$ equals zero. The remainder is divided into 48 compartments distributed along the $V_A/Q$ coordinate. This value is stored in the memory.

The total cardiac output ($Q_T$) of the patient is then measured using conventional measurement techniques, and this value is stored in RAM. Using this value, the actual blood flow, $Q_C$, to the lung is determined, such that the value of $Q_C$ equals $FQ \times Q_T$. This value is also stored in RAM.

From the MIGT program, the inspired oxygen and the carbon dioxide concentrations are measured for the patient and stored in memory. The alveolar and capillary blood pressure, $PO_2$ and $PAO_2$, respectively, are then calculated for each for each of the 50 compartments and stored in memory.

The mixed venous gas combination ($PVO_2$) of the patient is then measured. Using the measured value, which is stored in RAM, the stimulus for hypoxic constriction ($PSO_2$) for each compartment can be calculated as:

$$PSO_2 = PVO_2^{.4} \times PAO_2^{.6}$$

and the values are stored in RAM. For each compartment, the overall gas exchange for the entire lung is then calculated.

From the pulmonary circulation model, because the value for $PSO_2$ and other parameters are known, the relationship between pressure and flow (P/Q) for each compartment can be calculated as a curve and expressed as a quintic equation. Thus, the pressure flow (P/Q) equation for each of the 50 compartments is calculated and stored. The value is a function of the fractional flow (FQ) to each of the compartments.

Utilizing the MIGT technique, the flow to each compartment as a fraction $$FQ = \frac{Q_C}{Q_T}$$

is determined. This value is stored in the memory. Using the circulation model, the flow to each compartment is expressed as a relative flow (RQ) where $$RQ = Q_C/Q_{CN},$$

where $Q_C$ is the actual measured values for the patient set forth above, and $Q_{CN}$ is the flow to that compartment in the absence of hypoxic constriction and with a normal cardiac output.

If the cardiac output measured is not normal, a differential value (DQ) is calculated as $DQ = Q_T/Q_{TN}$, where $Q_{TN}$ is the summation of the normal flows to all 50 compartments in the absence of hypoxic pulmonary vasoconstriction.

Having calculated the quintic equation for all compartments, an arbitrary pulmonary artery pressure (PAP) is then assumed for the patient and each equation solved for the RQ that corresponds to that pulmonary artery pressure. As noted above, the values of RQ are a function of the pulmonary artery pressure. Because the $Q_C$ is known for each compartment and because $Q_{CN} = Q_C/RQ$, therefore:

$$\sum_{1}^{x} Q_C$$

can be calculated and multiplied by the differential value DQ. If this value equals $Q_T$, then the procedure is stopped and the optimal PAP pressure for the patient can be determined. If the value of PAP does not yield an RQ such that $$\sum_{1}^{x} Q_{CN} \times DQ = Q_T$$

the PAP is adjusted iteratively and recalculated until:

$$\sum_{1}^{x} Q_{CN} \times DQ = QT$$

The resulting value is the unique value for the PAP that satisfies both the $V_A/Q$ and P/Q requirements for all compartments. Once this value is determined, a treatment regimen is then determined for the patient. For example, the patient can inhale nitric oxide with an infusion of an intravenous vasoconstrictor such as almatrine or a prostacyclin analog. With NO and the intravenous vasoconstrictors used simultaneously the patient's pulmonary artery pressure is reduced while pulmonary gas exchange is optimized.

Figure 7:
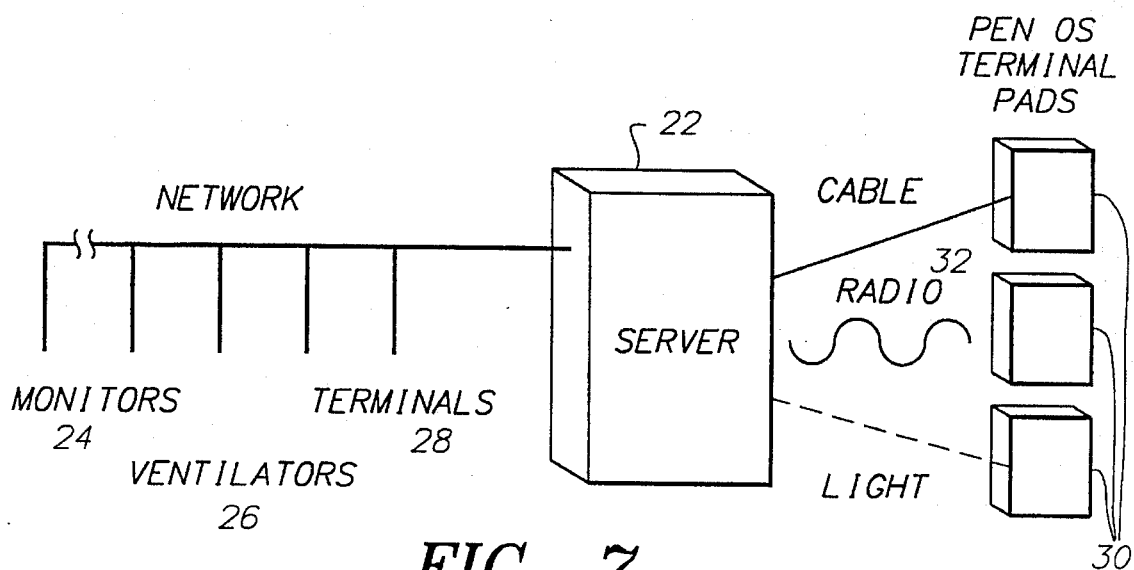
FIG. 7 is an enhanced block diagram of the present invention.

FIG. 7 is a block diagram of a more preferred configuration for a system to be placed in an intensive care unit. The hardware comprises a server 22 for data collection and database management. The server is connected to a network of monitors 24, ventilators 26 and terminals 28. In this embodiment the user interfaces comprise operating tablet computers 30. Using server 22, the tablet computers 30 can be directly cabled to the server or, alternatively, may communicate via radio waves or infrared light 32.

Figure 8:
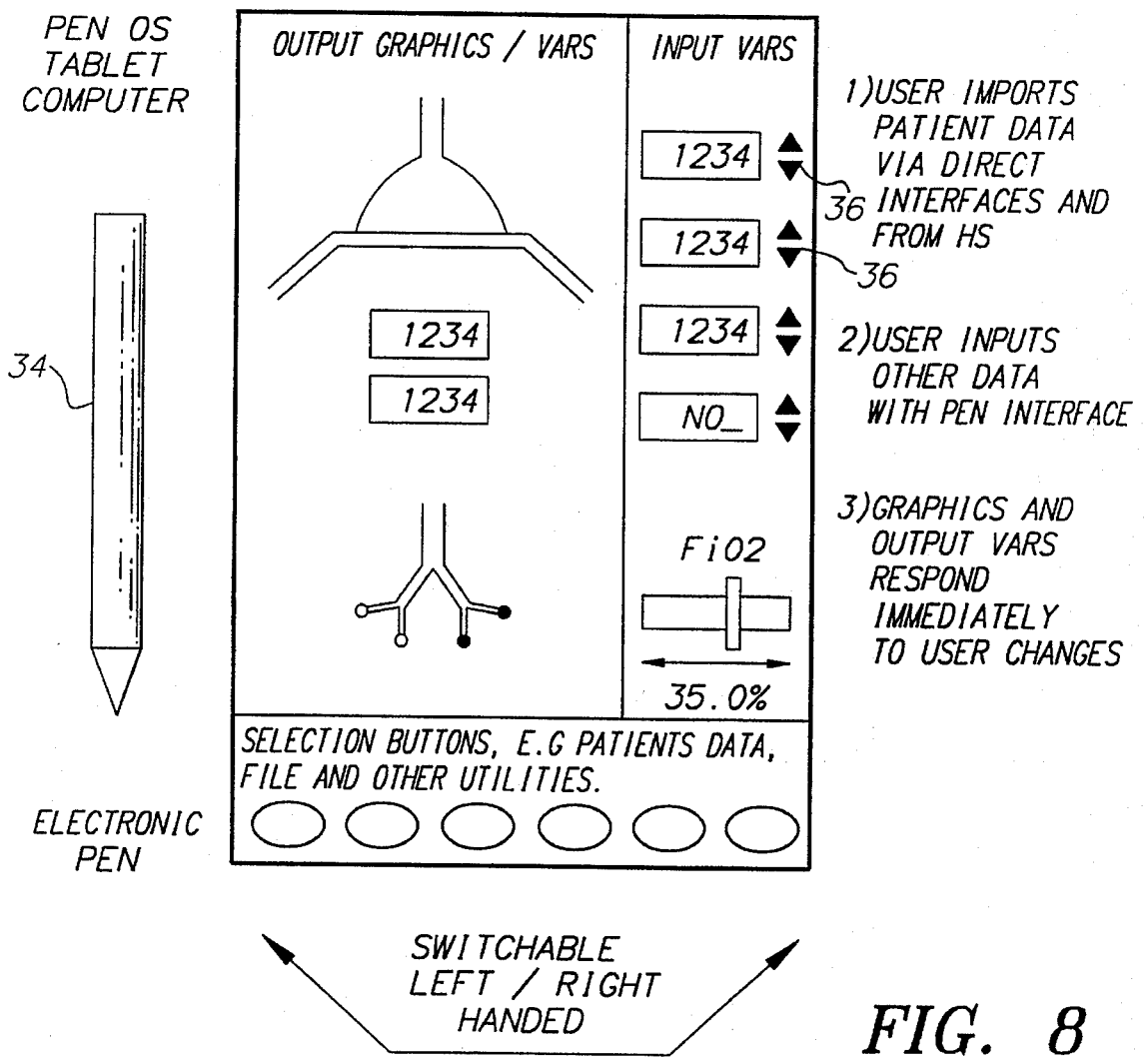
FIG. 8 is a perspective view of a more preferred apparatus in accordance with the present invention.

FIG. 8 comprises a direct manipulation reversible feedback interface to be used in accordance with the embodiment of FIG. 7. In this embodiment a user could download a snapshot of patient data in a moment in time and then alter variables using the pen input device 34. This data would include data, such as heart rate, blood pressure, alveolar pressure and hematocrit. A plurality of input arrows 36 could be used to change the values of variables. Changes would immediately be reflected in changes to graphic images and textual outputs.

Figure 9:
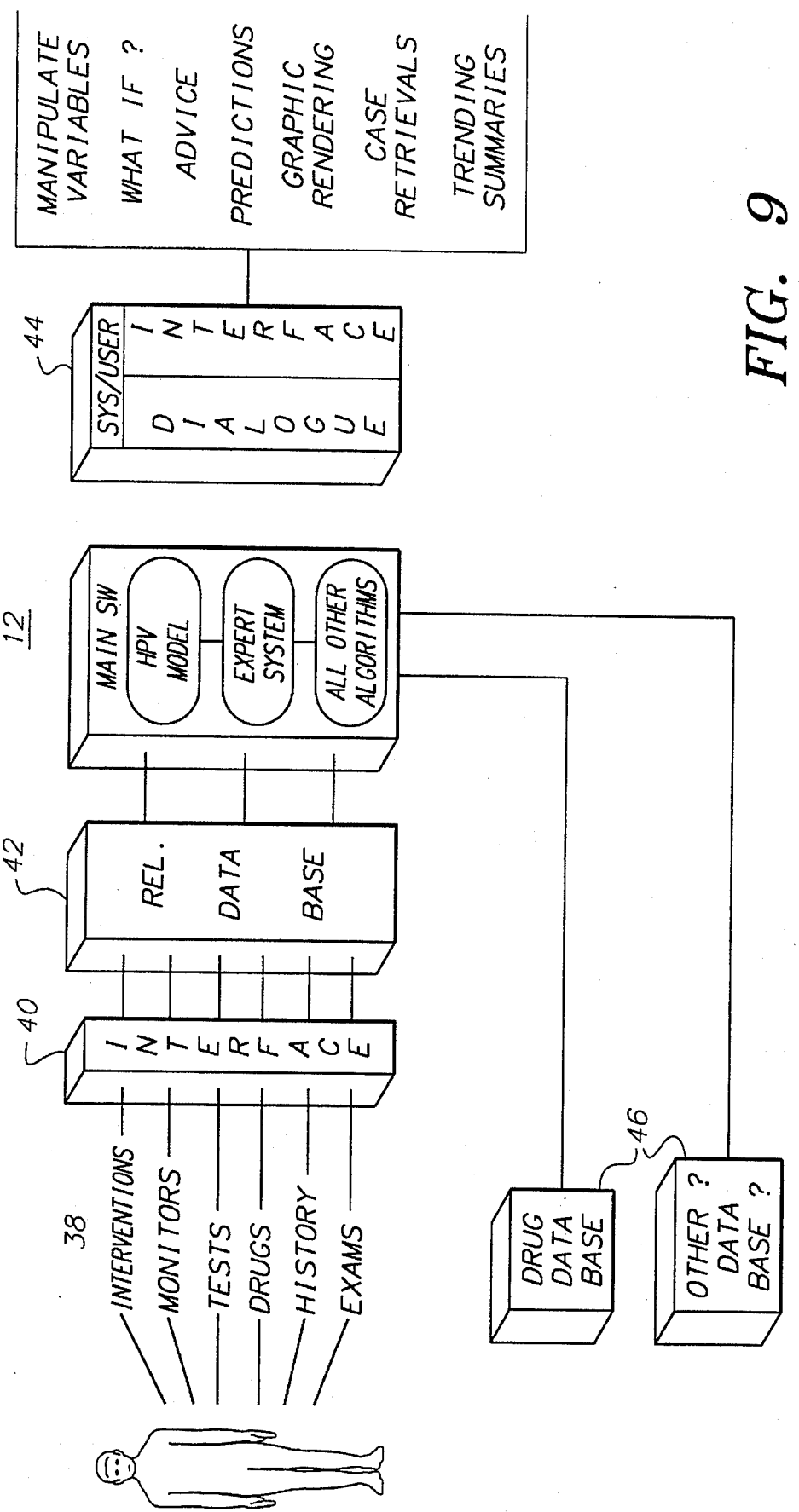
FIG. 9 is a perspective view of yet a further preferred embodiment in accordance with the present invention.

Another embodiment of the present invention is shown with respect to FIG. 9. Referring to FIG. 9, the present invention is utilized with a series of monitors 38 which measure key medical variables of the patient including interventions, monitors, tests, drugs, history and examinations. These variables are connected to an interface 40 and a relational database 42 and software in accordance with the present invention. As noted above, the ROM includes an HPV model, expert system, system algorithms including the program described in FIG. 10, and may access other databases 46. The invention incorporates a system/user interface 44 which permits querying.

The present invention is now described in the context of an operative example in view of the Figures and most particularly FIGS. 5–10B. Initially, the physical condition of the patient is monitored and key variables are measured. These measured variables which include are stored in the memory. The mean and standard deviation for the log V/Q for each of 50 compartments of the patient is determined. These values are stored in the RAM. The fractional flow (FQ) to each compartment is then calculated and stored. The cardiac output of the patient measured and from this value, an actual flow ($Q_{+sc\ c}$) is calculated for each compartment whereby $Q_{+sc\ c}$=FQ·QT. The inspired oxygen and carbon dioxide concentrations are measured. These values are stored in the RAM. The mixed venous gas combination for the patient is determined and stored. From this value, the stimulus for hypoxic pulmonary vasoconstriction ($PSO_2$) for each of compartments is determined. Given the $PSO_2$ and other variables, the pressure/flow relationship is determined for each of the 50 compartments. These values are stored in memory. The flow to each compartment as a fraction is determined. The flow to each compartment is expressed as a relatively flow.

If the cardiac output measured is abnormal, a differential value (DQ) is calculated. The value for the quintic equation for all compartments is determined and an arbitrary pulmonary artery pressure is assumed. The value of RQ is solved. The pulmonary artery pressure is adjusted iteratively until it satisfies both the V/Q and P/Q requirements. Thus, the patient's condition is determined and a treatment regimen is determined for the patient based upon the need to vary pulmonary artery pressure.

The present invention has been described in the context of the preferred embodiment described herein. It is to be noted that the true nature and scope of the present invention is to be determined with reference to the claims appended hereto.

What is claimed is:

1. A method for combining the ventilation/perfusion ratio and pulmonary pressure/flow relationship of a patient comprising the following steps:

determining an initial health condition of a patient so as to define a pulmonary pressure/flow curve for each of a plurality of individual lung compartments of said patient and for the total lung;

applying a stimulus of hypoxic pulmonary vasoconstriction to the pressure flow curve for each individual compartment to obtain a pressure flow curve for each of said plurality of compartments; and deriving a pulmonary artery pressure value corresponding to a ventilation/perfusion ratio that satisfies both the individual compartment and total lung pressure flow requirements for each of said pulmonary pressure/flow curves.

2. The method of claim 1 wherein the pulmonary pressure/flow relationship and ventilation/perfusion ratio for each of said plurality of compartments are altered and the steps of claim 1 are repeated such that of each said pulmonary artery pressure values is altered.

3. The method of claim 1 wherein said plurality of compartments comprises about 49 compartments.

4. The method of claim 2 wherein each of the steps of claim 2 is repeated iteratively until the pulmonary artery pressure values is altered by less than about 0.1%.

5. A method for combining a ventilation/perfusion ratio and a pulmonary artery pressure for a patient comprising the following steps:

determining a fractional flow of blood to each of a plurality of lung compartments of said patient, said fractional flow being based upon a ventilation/perfusion ratios for each of said plurality of lung compartments;

determining a total cardiac output of said patient;

calculating an actual blood flow to each of said plurality of lung compartments, said actual blood flow equalling the total cardiac output multiplied by the fractional flow of blood to each compartment;

determining alveolar and capillary blood oxygen partial pressures for each of said plurality of lung compartments;

determining a stimulus for hypoxic pulmonary vasoconstriction for each of said plurality of compartments and an overall gas exchange value for the entire lung of said patient;

determining a pressure flow relationship based upon said stimulus for hypoxic pulmonary vasoconstriction;

calculating a total cardiac output for the patient in the absence of hypoxic pulmonary vasoconstriction; and determining a pulmonary artery pressure value such that the normal blood flow to each said compartment equals the summation of the compartmental blood flows.

6. The method of claim 5 wherein the actual blood flow and ventilation/perfusion ratio for each of said plurality of compartments are altered and the steps of claim 1 are repeated such that the pulmonary artery pressure value is altered.

7. The method of claim 5 wherein said plurality of compartments comprises about 49 compartments.

8. A method for linking a ventilation/perfusion ratio and a pressure flow model of a patient comprising the following steps:

determining a fractional flow of blood to each of a plurality of lung compartments of the patient based upon an average and standard deviation for a logarithm of a ventilation for each of a plurality of compartments of a lung;

measuring a total cardiac output of the patient;

determining an actual blood flow to the patient's lung as equalling the total cardiac output multiplied by the fractional flow;

determining the alveolar and capillary blood pressures of each of said lung compartments;

determining a stimulus for hypoxic pulmonary vasoconstriction for each of said plurality of lung compartments;

determining an overall gas exchange for the entire lung;

determining a pressure/flow relationship based upon said stimulus for hypoxic pulmonary vasoconstriction;

calculating a total cardiac output for said patient in the absence of hypoxic pulmonary vasoconstriction;

determining a pulmonary artery pressure value such that the normal blood flow to each said compartment equals the summation of the blood flowing to each of said compartments.

9. A method for combining a ventilation/perfusion ratio and a pressure flow for a patient in pulmonary distress:

determining a fractional flow of blood to each compartment of approximately 49 lung compartments of the patient based upon an average and standard deviation for the logarithm of a ventilation/perfusion ratio for each of said lung compartments of the patient, and a pulmonary artery pressure value of said lung;

determining an actual blood flow to said lung as equalling a total cardiac output times said fractional flow;

determining a stimulus for hypoxic pulmonary vasoconstriction for each of said lung compartments and an overall gas exchange for an entire lung;

determining a pressure flow relationship for said patient based upon the stimulus for hypoxic pulmonary vasoconstriction;

determining a total cardiac output in the absence of hypoxic pulmonary vasoconstriction;

altering the pulmonary artery pressure of said patient using a vasodilator such that the summation of the cardiac output for each compartment equals total blood flow.

10. The method of claim 9 wherein said vasodilator comprises nitric oxide by inhalation or infusion.

11. Apparatus for defining a pulmonary artery pressure of a patient comprising:

first monitor means for measuring a ventilation/perfusion ratio for each of a plurality of lung compartments for said patient;

second monitor means for determining a cardiac output of said patient;

processor means under the control of a prestored computer program for determining a fractional blood flow to each of said lung compartments of a said patient, and stimulus for hypoxic pulmonary vasoconstriction of each of said plurality of lung compartments, a pressure and flow equation for each of said compartments;

memory means for storing said fractional blood flow, said stimulus for hypoxic pulmonary vasoconstriction, and said pressure and flow equation for said compartments and a normal cardiac output value of said patient;

said processor further determining a relative flow of blood to said lung compartment as a ratio of an actual flow of blood, and determining a value for relative flow such that the sum of a normal flow times said ratio equals total flow, said value for relative flow being a function of pulmonary artery pressure.

* * * * *